United States Patent [19]

Schudel et al.

[11] Patent Number: 4,713,473

[45] Date of Patent: Dec. 15, 1987

[54] PROCESS FOR TREATING 2-ETHYLHEXYL P-METHOXYCINNAMATE IN THE PRESENCE OF A PHENOL

[75] Inventors: Peter Schudel, Grüt; Rolf Schwarzenbach, Winterthur; Hans U. Gonzenbach, Geneva, all of Switzerland

[73] Assignee: Givaudan Corporation, Clifton, N.J.

[21] Appl. No.: 1,279

[22] Filed: Jan. 8, 1987

[30] Foreign Application Priority Data

Jan. 15, 1986 [CH] Switzerland .......................... 128/86
Oct. 16, 1986 [CH] Switzerland ......................... 4137/86

[51] Int. Cl.$^4$ ............................................. C07C 69/76
[52] U.S. Cl. .................................................... 560/053
[58] Field of Search ......................................... 560/053

[56] References Cited

PUBLICATIONS

Zeiger, E. et al., Environ. Mutagen 7(2) 213–232, 1985.
Bonin, A. M. et al., Mutat. Res. 105(5), 303–308, 1982.

*Primary Examiner*—Paul J. Killos
*Attorney, Agent, or Firm*—Robert F. Tavares; Linda A. Vag

[57] ABSTRACT

A process for treating 2-ethylhexyl p-methoxycinnamic acid ester is described. The process comprises heating, preferably distilling, the ester in the presence of a phenol to insure that the ester is considered Ames negative.

7 Claims, No Drawings

PROCESS FOR TREATING 2-ETHYLHEXYL P-METHOXYCINNAMATE IN THE PRESENCE OF A PHENOL

BACKGROUND OF THE INVENTION

2-Ethylhexyl p-methoxycinnamate, 1, is a known sunscreen agent which absorbs ultraviolet radiation in the UV-B range.

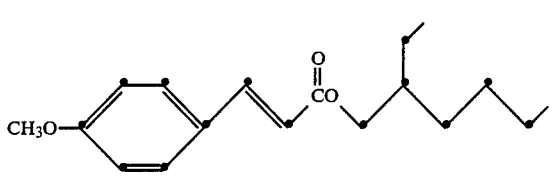

The ester may exist as the E- or Z-isomer or as a mixture of these isomers.

There are two major processes for the manufacture of 2-ethylhexyl p-methoxycinnamate. The first involves condensation of p-methoxybenzaldehyde with the acetate of 2-ethylhexanol as follows:

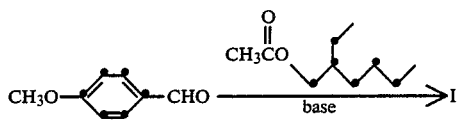

The second involves condensation of p-methoxybenzaldehyde with methyl acetate followed by a transesterification with 2-ethylhexanol, as follows:

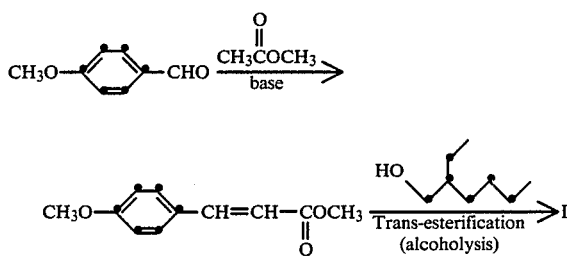

In either case the crude material is usually distilled in order to separate the desired product 1 from other reaction materials in the crude material such as unreacted starting material. Another purpose of the distillation step is to obtain material which is free from undesirable odors since the ester 1 is used predominately in cosmetic and sunscreen preparations applied directly to the skin.

It has been reported recently that certain samples of this ester can test positive in the Ames test. [See for example A. M. Bonin et al., Mutation Research 105 (1982), 303–308.] The Ames test is a procedure developed by Ames et al. to screen chemicals for potential mutagenicity. [See for example B. N. Ames et al., Mutation Research 31 (1975), 347–364.] The test specimen is a bacterial defective mutant which is known to revert to the normal mutant (wild type) under the influence of mutagens.

A. M. Bonin et al., loc. cit., expressed the theory that a trace component which is sometimes present in the 2-ethylhexyl p-methoxycinnamate may be responsible for the occurence of an Ames positive reaction. Its nature or existence is, however, unreported. A need exists, therefore, to find a method which insures that any 2-ethylhexyl p-methoxycinnamate which is produced for sale and use will not test positive when subjected to the Ames test. The invention described herein fills that need.

THE INVENTION

It has now been found that heating, preferably distilling, 2-ethylhexyl p-methoxycinnamate in the presence of a phenol can be used as a reliable procedure to insure that the product manufactured will not test Ames positive. It is not known how the procedure works or whether it prevents the formation of, destroys, or renders inactive whatever it is that would cause a positive reaction to occur. This invention, therefore, concerns a process for the treatment of 2-ethylhexyl p-methoxycinnamate which comprises heating, preferably distilling, the ester in the presence of a phenol in order to insure that a product will be produced which does not test positive in the Ames test, i.e. the mutagenic factor, or Ames factor, is such that the material is considered Ames negative.

In the preferred process the distillation that is used to separate the desired 2-ethylhexyl p-methoxycinnamate from the starting materials and by-products can be conducted over a phenol so as to rectify and, in the same step, insure that the Ames factor is such that the material is considered Ames negative.

DESCRIPTION OF THE PREFERRED EMBODIMENTS

Any compound having a phenolic group, can be used in the process of this invention. Among the phenols contemplated are phenols of the structure:

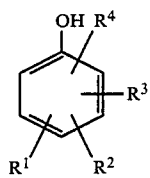

wherein (a) $R^1$, $R^2$ and $R^3$ are the same or different and represent hydrogen, an alkyl group of one to twelve carbon atoms, an alkenyl group of two to twelve carbon atoms, an alkoxy group of one to six carbon atoms, a hydroxy group or aryl group such as phenyl or naphthyl, and (b) $R^4$ represents hydrogen or the substituent $—(CH_2)_n—COOR$ in which R is hydrogen or an alkyl group of one to eighteen carbon atoms and n is 0, 1, 2, 3 or 4 or the substituent $—(CH=CH)_n—COOR$ in which R is hydrogen, phenyl, benzyl or an alkyl group of one to eighteen carbon atoms and n is 0, 1 or 2.

The substituents $R^1$, $R^2$ and $R^3$ can be present in the o-m- or p-position. The alkyl, alkenyl and alkoxy substituents can be linear or, preferably, branched. It is preferred that one of the groups, $R_1$, $R_2$, $R_3$ or $R_4$ not be hydrogen.

It is particularly preferred to use a phenol in which one or more of the hydrogen atoms on the aromatic ring, preferably in one or both ortho-positions or para-position is/are replaced by the same or different alkyl groups. Examples of such alkylphenols are cresols (o-, m-, p-) and xylenols (2,3-; 2,4-; 2,5-; 2,6-; 3,4-; 3,5-dimethylphenol), 4-tert.butylphenol, 2,6-di-tert.butylphenol and derivatives thereof, 2,6-di-tert.butyl-p-cresol, thymol (2-isopropyl-5-methylphenol) and carvacrol (2-p-cymenol), 2-isopropenyl-5-methylphenol as well as 4-tert.octylphenol, the nonylphenols and the dodecylphenols, di-tert.butyl-hydroxy-toluene (BHT), tert.butyl-hydroxy-anisole (BHA), and tert. butyl-hydroquinone (TBHQ).

Examples of other phenols, encompassed by formula II, or having the structural principle of formula II, which may also be suitably used are as follows. (As with the above alkylphenols, those in which the substituents are in the ortho- or para-positions are preferred.)

(a) Gallic acid and its derivatives [e.g. esters such as (lower) alkyl esters, ethers such as (lower) alkyl ethers, etc];

(b) Polycyclic phenols, e.g. 2- or 3-ringed, with the structural principle of formula II, e.g. tocopherols; or (c) Complex molecules with the structural principle of formula II, e.g. the o- m- or p-derivatives of 2,6-di-t-butylphenol such as e.g.

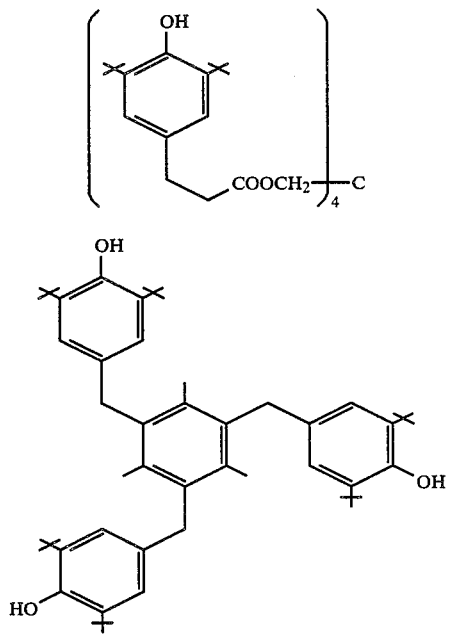

(d) o-, m- or p-Hydroxycinnamic acids or o-, m- or p-hydroxycinnamic acid esters, especially those in which the ester is phenyl, benzyl or a $C_1$ to $C_{18}$ alkyl group including cyclohexyl. The phenyl ring of the acid can also be o-, m- or p-substituted with an alkyl group, e.g. a $C_1$ to $C_4$ alkyl group, such as methyl, ethyl, propyl or butyl. The alkyl ester is especially a $C_1$ to $C_8$ alkyl ester.

Especially preferred for use in the process of this invention are the hindered phenols di-tert.butyl-hydroxy-toluene (BHT), tert.butyl-hydroxy-anisole (BHA) and tert.butyl-hydroquinone (TBHQ).

As stated above, the invention may be carried out by simple heating or preferrably by distillation. The method of distillation is not critical. Although, of course, even simple distillations such as rectilinear distillation, parallel flow distillation and descending distillation, can be used e.g. on a laboratory scale, column distillation (rectification) is preferred on an industrial scale. In this case there can be employed the columns which are usually used for this purpose, namely for example.

plate columns, e.g. perforated plate columns, etc.,
spray columns,
spinning band columns,
spraypack columns,
slotted tube columns, and
packed columns, etc.

The material from which these columns are constructed is not critical and is conveniently glass, quartz glass, stainless steel, ceramics, polymeric synthetic material, e.g. fluorinated synthetic material. Columns having column filings of stainless steel, e.g. of the meshpack type (namely geometrically arranged packing), are preferably used.

The rectification can be carried out, either continuously or discontinuously. It is preferably carried out under reduced pressure, e.g. a pressure of about 0.1 to 5 mbar, especially about 0.1 to 2 mbar.

The distillation is conveniently carried out in a temperature range of about 150° C. to about 230° C., especially from about 170° C. to 200° C.; the ester, I, then has the following data:

Boiling point 185°–195° C./1 mbar
140°–150° C./0.1 mbar.

The rate of distillation is not critical and depends especially on the size and type of installation; it is usually slow at the beginning of the distillation and can be increased after separating the first runnings in the usual manner. [See also Römpps Chemielexikon, 8th edition, Franckh'esche Verlangshandlung, Stuttgart (1981), volume 2, Distillation, columns].

The amount of phenol to be added in the distillation is not critical. However, it conveniently amounts to only about 0.01 to 2 wt.%, especially about 0.05 to 0.5 wt.%, of I.

The phenol is conveniently added to the distillation material in the form of a concentrated solution, e.g. a 10% to 40% solution in a suitable solvent, conveniently a polar high boiling solvent or, preferably, dissolved in the ester, I, itself. The addition of a liquid phenol can, however, also be carried out in undiluted form, e.g. by injection. The continuous addition is preferred.

While it is preferred to distill the 2-ethylhexyl p-methoxycinnamate in the presence of a phenol, it is not necessary to carry out a distillation to practice this invention. Simply heating 2-ethylhexyl p-methoxycinnamate at a suitable temperature for a suitable length of time in the presence of a phenol will provide a 2-ethylhexyl p-methoxycinnamic acid which tests Ames negative.

The temperature, duration of heating, amount of phenol and choice of phenol will be expected to be interdependent. It is well within the skill of an ordinary practitioner in the art to determine a suitable temperature, heating period and amount of phenol to produce a product which tests Ames negative.

The convenient parameters in the case of the simple heating of the cinnamate I are:

| | |
|---|---|
| Amount of phenol: | 0.05–2 wt. %, especially 0.1–1 wt. % |
| Temperature: | 150–230° C., preferably 170–200° C. |
| Period: | several hours, e.g. 3–30 hours especially 6–20 hours |
| Pressure: | atmospheric pressure, excess pressure or reduced pressure |

| | |
|---|---|
| Vessel: | not critical |
| Atmosphere: | not critical, but an inert atmosphere is preferred. |

EXAMPLES

AMES TEST

The following procedure was used for performing the Ames test on the examples that follow:

Microorganism Used:

Histidine-requiring strain ("bacterial tester strain"); Salmonella typhimurium TA 1538

Cultures Used:

(a) Deep-frozen stock culture ("frozen permanents") in nutrient solution NB (see below), 8% DMSO, storage at −80° L C.

(b) Agar slant subcultures with nutrient agar NBA after incubation for 24 hours at 37° C. with the usual spontaneous frequency range of up to 30 colonies per plate [see Maron and Ames, Mutation Res. 113 (1983), 173–215].

Storage at 4° C., periodic testing in this respect for spontaneous frequency range, UV sensitivity and crystal violet sensitivity in accordance with Maron and Ames, ioc cit., pages 179/180.

(c) Test cultures: growth overnight in nutrient solution NB at 37° C. in a shaking water bath. Cell density $1-2 \times 10^9$ cells$\times$ml$^{-1}$ determined by plating-out a suitable dilution on complete medium MBA.

Media Used:

(a) Nutrient medium NB: 24 g/l of nutrient solution Oxoid No. 2 [Oxoid Ltd. Basingstoke, Hants, GB] (complete medium), (b) Nutrient agar NBA: NB+15 g/l of Difco Bacto Agar [Difco Laboratories Detroit, Mich.], (c) Vogel-Bonner Minimal Agar plates [Gibco Ltd., P.O. Box 35 Paisley, Scotland] (histidine-free)

1 liter contains:

| | |
|---|---|
| 20 ml of the following salt solution: 10 g of MgSO$_4$ × 7H$_2$O 109 g of citric acid × 1H$_2$O 500 g of K$_2$HPO$_4$ 175 g of NaNH$_4$HPO$_4$ × 4H$_2$O 670 ml of H$_2$O | heated in an autoclave for 20 minutes to 120° C. |
| glucose: | 20 g/l filtered sterile |
| Difco Bacto Agar: | 15 g/l |
| (d) Soft agar ("Top Agar"): | NaCl 5.0 g/l Difco Bacto Agar 7.0 g/l 0.05 mM of biotin 0.05 mM of L-histidine (as the "starter") |

Test procedure Used:

The samples of the ester I to be investigated are diluted with dimethyl sulphoxide in glass test tubes so that the following concentration series result: 750 μl [I]/ml, 500 μl [I]/ml, 300 μl [I]/ml, 100 μl [I]/ml and 30 μl [I]/ml.

In each case 0.1 ml thereof is pipetted into 2.0 ml of liquid soft agar (water bath temperature 45±1° C.) so that in each small glass the ester I is present in amounts of 75 μl, 50 μl/ 30 μl, 10 μl and 3 μl.

0.1 ml of the culture (c) is added to these small glasses and each of the small glasses are immediately added to Petri dishes of diameter 8.5 cm (containing 20 ml of Vogel-Bonner Minimal Agar). 4 Petri dishes are plated-out per individual dilution. After solidification of the upper agar layer the dishes are inverted and incubated for 2 days at 37° C. 2 days after the plating-out the visible colonies are counted with the naked eye.

As controls there are used dishes prepared using only in each case 0.1 ml of DMSO and 0.1 ml of TA 1538 in place of the dilution series.

There are defined:

| MF* (mutation frequency) | Number of colonies in the samples [1] Number of colonies in the control |
|---|---|
| "Ames positive" | At least double the number of colonies when compared with the control |
| "Ames negative" | The test plate contains less than double the amount of colonies of the control. |

*The term Ames factor is used in this application to designate mutation frequency.

EXAMPLE 1

The following procedure was carried out on a sample of 2-ethylhexyl p-methoxycinnamate (ester I) which was known to test Ames positive to illustrate the preferred embodiments of this invention. (The sample used here for purposes of illustration has a higher Ames factor than a normal sample to be used, most of which are Ames negative before the distillation begins.) The results are given in the table below.

5 kg of ester I are added to 10 liter 4-necked flask which is provided with a capillary, thermometer, dropping funnel and distillation column. The column, has a height of 2.30 m and a diameter of 70 mm and is filled with meshed wire of the SULZER BX inox type. At the head of the column the return ratio can be regulated from 1:5 at the beginning of the distillation to 1:1 towards the end of the distillation. 75 g of a 33% solution of butylhydroxyanisole (BHA) are added continuously as the hindered phenol over the entire distillation period of 6 hours. The pressure amounts to about 1 mbar at the head of the column, the temperature in the still amounts to 216° C. Fractionation is carried out to give fractions of about 500 g, which fractions are submitted to a gas-chromatographical analysis and, moreover, are evaluated with respect to odor. The organoleptically acceptable fractions contain more than 98% of ester I in accordance with gas-chromatographical analysis and are combined at the end.

Ames test

| | | Results | | | | | |
|---|---|---|---|---|---|---|---|
| Experiment | | | | MF value | | | |
| No. | Additive | μl[I]/plate | 3 | 10 | 30 | 50 | 75 |
| 1 | — | Ester 1* | 3.0 | 6.8 | 15.2 | 13.0 | 12.0 |
| 2 | BHT | Ester 1 | 0.8 | 0.6 | 0.6 | 0.8 | 1.0 |
| 3 | BHA | Ester 1 | | 1.0 | 1.0 | 1.8 | |

*Starting material for experiments 2 and 3.

The samples treated in experiments 2 and 3 are clearly negative to the Ames test.

EXAMPLE 2

If the ester I*, in which 0.5% of BHT are homogeneously dissolved, is heated in an open vessel for 6 hours to 180° C., there are obtained analogous results as in the case of the distillation.

Ames Test

| Experiment No. | Additive | μl[1]/plate | Results MF value | | | | |
|---|---|---|---|---|---|---|---|
| | | | 3 | 10 | 30 | 50 | 75 |
| 1 | BHT | Ester 1* | 3.0 | 6.8 | 15.2 | 13.0 | 12.0 |
| 4 | BHT | Ester 1 150° C./8 h | 1.4 | 2.2 | 3.2 | 3.4 | 2.6 |
| 5 | BHT | Ester 1 150° C./16 h | 1.0 | 1.6 | 3.0 | 2.8 | 1.6 |
| 6 | BHT | Ester 1 180° C./8 h | 0.8 | 0.8 | 1.4 | 1.0 | 1.0 |

*Starting material for experiments 4, 5 and 6.

Experiment 6 produces a product which is clearly Ames negative. Examples 4 and 5 help to illustrate the effect of temperature and heating time on the process of this invention in reducing the Ames factor of any sample.

EXAMPLE 3

In each of the following series of experiments 75 g of ester I** were treated with 0.5 wt.% of a phenol and distilled in a flask provided with a boiling capillary and distillation bridge. The boiling temperature was 160±5° C., the bath temperature was 195°–215° C. and the vacuum was 0.2–0.25 mmHg. The yields were quantitative; the distillates were subjected to an Ames test.

Ames Test

| Experiment No. | Additive | μl[1]/plate | Results MF value | | | | |
|---|---|---|---|---|---|---|---|
| | | | 3 | 10 | 30 | 50 | 75 |
| 7 | — | Ester 1** | 4.3 | 12.2 | 27.3 | 30.2 | 20.8 |
| 8 | Hydroquinone | Ester 1 | 1.2 | 0.8 | 2.0 | 2.0 | 1.2 |
| 9 | TBHQ | Ester 1 | 0.8 | 1.8 | 2.3 | 1.7 | 1.5 |
| 10 | p-Hydroxycinnamic acid 2-ethylhexyl ester | Ester 1 | 1.3 | 1.7 | 2.5 | 2.3 | 2.5 |
| 11 | Gallic acid propyl ester | Ester 1 | 0.7 | 0.5 | 0.2 | | |
| 12 | Gallic acid octyl ester | Ester 1 | 0.8 | 1.0 | 1.2 | 0.8 | 1.0 |
| 13 | Gallic acid dodecyl ester | Ester 1 | 1.0 | 1.7 | 2.0 | 2.3 | 2.0 |
| 14 | p-Hydroxy-m,m-di-tert.butylphenyl-propionic acid stearyl ester | Ester 1 | 1.3 | 2.0 | 2.5 | 2.3 | 1.7 |
| 15 | p-Hydroxycinnamic acid n-butyl ester | Ester 1 | 2.3 | 3.0 | 5.0 | 2.7 | 2.7 |
| 16 | p-Hydroxycinnamic acid methyl ester | Ester 1 | 2.3 | 3.7 | 4.7 | 2.3 | 2.7 |

**Starting material for experiments 8–16.

The series of experiments illustrates that a variety of phenols can be used to reduce the Ames factor for any sample of 2-ethylhexyl p-methoxycinnamate which causes the Ames positive test. While some phenols appear to be more effective than others, all were very effective when compared to the control.

We claim:

1. A process for the treatment of 2-ethylhexyl p-methoxycinnamate which comprises heating 2-ethylhexyl p-methoxycinnamate in the presence of a phenol at a temperature of from about 150° C. to about 230° C. for a time sufficient to provide a material which tests Ames negative.

2. A process according to claim 1 wherein the phenol has the formula

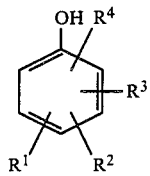

II wherein:

$R^1$, $R^2$ and $R^3$ are the same or different and represent hydrogen, an alkyl group of one to twelve carbon atoms, an alkenyl group of two to twelve carbon atoms, an alkoxy group of one to six carbon atoms, hydroxy or aryl, and $R^4$ represents hydrogen or the substituent —$(CH_2)_n$—COOR such that R is hydrogen or an alkyl group of one to eighteen carbon atoms and n is 0, 1, 2, 3, or 4 or the substituent —$(CH=CH)_n$—COOR in which R is hydrogen, phenyl, benzyl or an alkyl group of one to eighteen carbon atoms and n is 0, 1 or 2.

3. A process according to claim 2 wherein the phenol is present in an amount from about 0.01% to about 2% by weight of the 2-ethylhexyl p-methoxycinnamate.

4. A process according to claim 3 wherein the phenol is (a) an alkylphenol selected from the group consisting essentially of:

o-cresol, m-cresol, p-cresol,
2,3-dimethylphenol, 2,4-dimethylphenol,
2,5-dimethylphenol, 3,4-dimethylphenol,
3,5-dimethylphenol, 4-tert.butylphenol,
2,6-di-tert.butylphenol,
2,6-di-tert.butyl-p-cresol, thymol (2-isopropyl-5-methylphenol), carvacrol (2-p-cymenol), 2-isopropenyl-5-methylphenol,
4-tert.octylphenol, nonylphenol, dodecylphenol
di-tert.butyl-hydroxy-toluene (BHT),
tert.butyl-hydroxy-anisole (BHA), and
tert.butyl-hydroquinone (TBHQ); or, (b) is selected from the group consisting essentially of:

(i) o-hydroxycinnamic acid, m-hydroxycinnamic acid and p-hydroxycinnamic acid wherein the phenyl ring may be substituted in the o-, m- or p-position with an alkyl group containing from one to four carbon atoms, and, (ii) o-hydroxycinnamic acid esters, m-hydroxycinnamic acid esters, and p-hydroxycinnamic acid esters wherein (a) the phenyl ring may be substituted in the o-, m- or p-position with an alkyl group containing from one to four carbon atoms, and (b) the ester moiety is selected from the group consisting of alkyl groups containing from one to eighteen carbon atoms, phenyl or benzyl, (iii) gallic acid, gallic acid esters wherein the ester moiety is a lower alkyl group or gallic acid ethers wherein the ether moiety is a lower alkyl group.

5. A process according to claim 4 wherein the 2-ethylhexyl p-methoxycinnamate is distilled while heating at a pressure from about 0.1 mbar to about 5 mbar.

6. A process according to claim 5 wherein
(a) the temperature is from about 170° to about 200° C., and
(b) The phenol is present in an amount from about 0.05% to about 0.5% by weight.

7. A process according to claim 6 wherein the phenol is selected from the group consisting of di-tert.butyl-hydroxy-toluene (BHT), tert.butyl-hydroxy-anisole (BHA) and tert.butyl-hydroquinone (TBHQ).

* * * * *